(12) United States Patent
Gaudout et al.

(10) Patent No.: US 7,041,322 B2
(45) Date of Patent: *May 9, 2006

(54) PHLORIDZIN-RICH PHENOLIC FRACTION AND USE THEREOF AS A COSMETIC, DIETARY OR NUTRACEUTICAL AGENT

(75) Inventors: David Gaudout, Fougeres (FR); Denis Megard, St Brice en Cogles (FR); Claude Inisan, Rennes (FR); Christian Esteve, Cosse le Vivien (FR); Frédéric Lejard, Arradon (FR)

(73) Assignee: Diana Ingredients S.A., (FR)

( * ) Notice: Subject to any disclaimer, the term of this patent is extended or adjusted under 35 U.S.C. 154(b) by 178 days.

This patent is subject to a terminal disclaimer.

(21) Appl. No.: 10/105,040

(22) Filed: Mar. 22, 2002

(65) Prior Publication Data

US 2003/0003120 A1 Jan. 2, 2003

(30) Foreign Application Priority Data

Mar. 23, 2001 (FR) .................................. 01 03968

(51) Int. Cl.
 A61K 35/78 (2006.01)
 A61K 7/00 (2006.01)
 A61K 9/14 (2006.01)
 A61K 31/70 (2006.01)
 A61K 31/05 (2006.01)

(52) U.S. Cl. ...................... 424/765; 424/401; 424/439; 424/489; 424/725; 424/777; 426/542; 426/615; 426/640; 426/648; 514/25; 514/731; 514/732

(58) Field of Classification Search ................ 424/725, 424/765, 777, 439, 489; 426/542, 615, 640, 426/648; 514/25, 731, 732
See application file for complete search history.

(56) References Cited

U.S. PATENT DOCUMENTS

| 3,436,407 | A |   | 4/1969  | Masquelier ............... 260/345.2 |
| 4,698,360 | A |   | 10/1987 | Masquelier .................. 514/456 |
| 5,110,801 | A | * | 5/1992  | Leveen et al. ................. 514/34 |
| 5,853,728 | A | * | 12/1998 | Tanabe et al. ............... 424/401 |
| 6,448,232 | B1 | * | 9/2002 | Ehrenkranz ................... 514/25 |
| 6,509,054 | B1 | * | 1/2003 | Haddad et al. ............. 426/615 |
| 2002/0142012 | A1 | * | 10/2002 | Lanzendorfer et al. ..... 424/401 |

FOREIGN PATENT DOCUMENTS

| EP | 0 283 349 |    | 9/1988 |
| EP | 0 348 781 |    | 1/1990 |
| EP | 0 657 169 |    | 6/1995 |
| EP |   657 169 A1 | * | 6/1995 |
| FR | 1 427 100 |    | 12/1965 |

(Continued)

OTHER PUBLICATIONS

Picinelli et al., "Polyphenolic pattern in apple tree leaves in relation to scab resistance", J. Agric. Food Chem., 1995, 43, 2273-2278.*

(Continued)

*Primary Examiner*—Sreenivasan Padmanabhan
*Assistant Examiner*—Marina Lamm
(74) *Attorney, Agent, or Firm*—William A. Simons; Wiggin and Dana LLP

(57) ABSTRACT

A phenolic fraction of fruit obtained from the Rosaceae family and also to the process for the specific extraction of this fraction. The phenolic fraction is rich in dihydrochalcones (phloridzin and phloretin) and may be used as a cosmetic, dietary, or nutraceutical preparation.

27 Claims, 5 Drawing Sheets

FOREIGN PATENT DOCUMENTS

| | | |
|---|---|---|
| FR | 2 092 743 | 1/1972 |
| FR | 2 372 823 | 6/1978 |
| FR | 2 643 073 | 8/1990 |
| FR | 2 799 121 A1 * | 4/2001 |
| FR | 2799121 A1 * | 4/2003 |
| GB | 1 541 469 | 2/1979 |
| WO | WO 96/18382 A1 * | 6/1996 |

OTHER PUBLICATIONS

Lu et al., "Identification and quantification of major polyphenols in apple pomace", Food Chemistry, 1997, 59, 187-194.*

Mangas et al., "Differentiation by phenolic profile of apple juices prepared according to two membrane techniques", J. Agric. Food Chem., 1997, 45, 4777-4784.*

Suarez et al., "Changes in phenolic composition of apple juices by HPLC with direct injection", J. Sci. Food Agric., 1998, 78, 461-465.* van der Sluis et al., "Activity and concentration of polyphenolic antioxidants in apple: effect of cultivar, harvest year, and storage conditions", J. Agric. Food Chem., 2001, 49, 3606-3613.*

F. Karadeniz et al., "Phenolic compounds in apple juice from different varieties", *Report of XII International Congress of Fruit Juice*, Interlaken, Switzerland, May 1996, pp. 265-275.

G. Papanga et al., "The polyphenolic content of fruit and vegetables and their antioxidant activities. What does a serving constitute?", *Free Rad. Rev.*, 30, 153-162 (1999).

P. Sanoner et al., "Polyphenolic profiles of French cider apple varieties", Poster(?) at *Polyphenols, Wine, and Health Symposium*, Bordeaux, France, Apr. 1999.

P. Sanoner et al., "Polyphenol profiles of French cider apple varieties", *J. Agric. Food. Chem.*, 47, 4847-4853 (1999).

* cited by examiner

PHLORIDZIN-RICH PHENOLIC FRACTION AND USE THEREOF AS A COSMETIC, DIETARY OR NUTRACEUTICAL AGENT

FIELD OF THE INVENTION

The present invention relates to a phenolic fraction from fruit and also to the process for obtaining this fraction. This extract rich in an antioxidant compound, phloridzin, can be used as a cosmetic, dietary or nutraceutical preparation.

BACKGROUND TO THE INVENTION

It is known that polyphenolic compounds are relatively widespread and in large amount in the plant kingdom. In the Rosaceae family in particular, the analysis of the polyphenols of apple has led to the identification of at least 37 phenolic compounds, the most abundant of which are chlorogenic acid, procyanidins B1 and B2, epicatechin, phloretin, phloridzin and p-coumaric acid. Some of these compounds have physiological properties such as antioxidant, anti-mutagenic, antiallergic, anticancer and antidiabetic properties, and the like.

There are many other polyphenol-rich products on the market, the most common being extracted from green tea, from grape seeds and from pine bark (U.S. Pat. No. 4,698, 360, EP A 348 781, EP A 283 349, FR A 1 427 100, FR A 2 092 743, FR A 2 643 073 and FR A 2 372 823). Patent EP A 0 657 169 has already disclosed the extraction of a polyphenolic fraction from unripe fruit (weighing from 3 to 10 grams) of the Rosaceae family. The polyphenolic fraction thus defined is characterized by a high content of derivatives of the hydroxycinnamic acid family (chlorogenic acid, caffeic acid, and p-coumaric acid), and of molecules from the flavanol family (catechin, epicatechin and procyanidin). Analysis by high performance liquid chromatography of an extract obtained from the juice of unripe fruit shows that phloridzin represents less than 7% by weight of the total phenolic compounds, and dihydrochalcones (phloridzin and phloretin) less than 9%.

Among the phenolic compounds, phloretin and its glycosylated derivative, phloridzin, are typical of apple and the other fruit of the Rosaceae family. In particular, phloridzin is found in large amount in the pips, but it is also present in apple juice and skin. Phloridzin has antioxidant activity allowing a cardiovascular protection similar to that of estrogens. Moreover, phloridzin is capable of acting on melanogenesis by activating a cascade of enzymes including tyrosinase, thus allowing increased protection against ultraviolet radiation. Phloridzin also has antidiabetic action by competitive inhibition of the sodium-dependent blood transport of metabolites such as glucose, galactose and the like. Phloridzin is also involved in inhibiting the growth of tumor cells by blocking the activity of protein kinase C.

However, in apple (homogenate or juice), the dihydrochalcones (phloretin and phloridzin) are present in small amount relative to the other polyphenols. Chlorogenic acid and the procyanidins are the major polyphenols in apples, whether these are cider apples or dessert apples, phloridzin and phloretin never representing more than 5% by weight of the total polyphenols of ripe cider apples (analysis of 15 different varieties) (FIGS. 1 and 2).

In the known polyphenolic extracts, the proportions between the various phenolic molecules are conserved relative to the proportions present in the various starting materials, with the exception of the polymeric procyanidins, which are lost or degraded during the extraction.

Polyphenolic extracts rich in hydroxycinnamic acids (caffeic acid, chlorogenic acid and coumaric acid) and in flavanols (catechin, epicatechin and procyanidins), and poor in dihydrochalcones (phloridzin and phloretin) are thus conventionally obtained (FIG. 3).

| Phenolic compound | Apple* in mg/L of juice or mg/kg of homogenate | Known polyphenolic extract of apple (in mg/g of powder) |
| --- | --- | --- |
| Caffeic acid | $\epsilon$ | 21.7 |
| Catechin | $\epsilon$ to 150 | 15.1 |
| Chlorogenic acid | 60 to 1200 | 161.0 |
| Procyanidins | 500 to 5000 | 69.6 ($B_1$ and $B_2$) |
| p-Coumaric acid | 1 to 150 | 9.3 |
| Epicatechin | $\epsilon$ to 1400 | 41.4 |
| Phloridzin | 6 to 100 | 32.7 |
| Quercitrin | $\epsilon$ | 1.9 |
| Phloretin | 5 to 100 | 9.5 |
| Total polyphenols (expressed as phloridzin equivalent) | | 483.4 |

$\epsilon$ = unquantifiable amount
*Values compiled from measurements on 15 varieties of cider apples and 3 varieties of dessert apples on 3 harvests.

Karadeniz F & Ekski A. Phenolic compounds in apple juice from different varieties. Report—Scientific Technical Com. Int. Fed. Fruit Juice Producers, (1996), 24, pp. 265–275.

Sanoner P., Guyot S., Mamet N. and Drilleau J. F. Polyphenolic profiles of French cider apples varieties. In 'Polyphenols, wines and health', symposium, Bordeaux, (14–16 Apr. 1999).

Sanoner P., Guyot S., Mamet N., Molle D. and Drilleau J. F. Polyphenol profiles of French cider apples varieties. J. Agric. Food Chem. (1999), 47, pp. 4847–4853.

There is only very little, if at all any, caffeic acid naturally present in apples. Caffeic acid is in fact probably a degradation product of chlorogenic acid (Fiedler, 1954, Arzneimittel-Forsch., 4, 41).

SUMMARY OF THE INVENTION

The Applicant has developed novel phenolic fractions, which constitute the subject of the invention.

A subject of the invention is also the process for obtaining this fraction.

Another subject consists of the uses of this fraction as a dietary or nutraceutical supplement, as a means of protection against ultraviolet radiation, or as a cosmetic composition.

Other objects will become apparent on reading the description and the examples which follow.

DETAILED DESCRIPTION OF THE INVENTION

Figure 1:
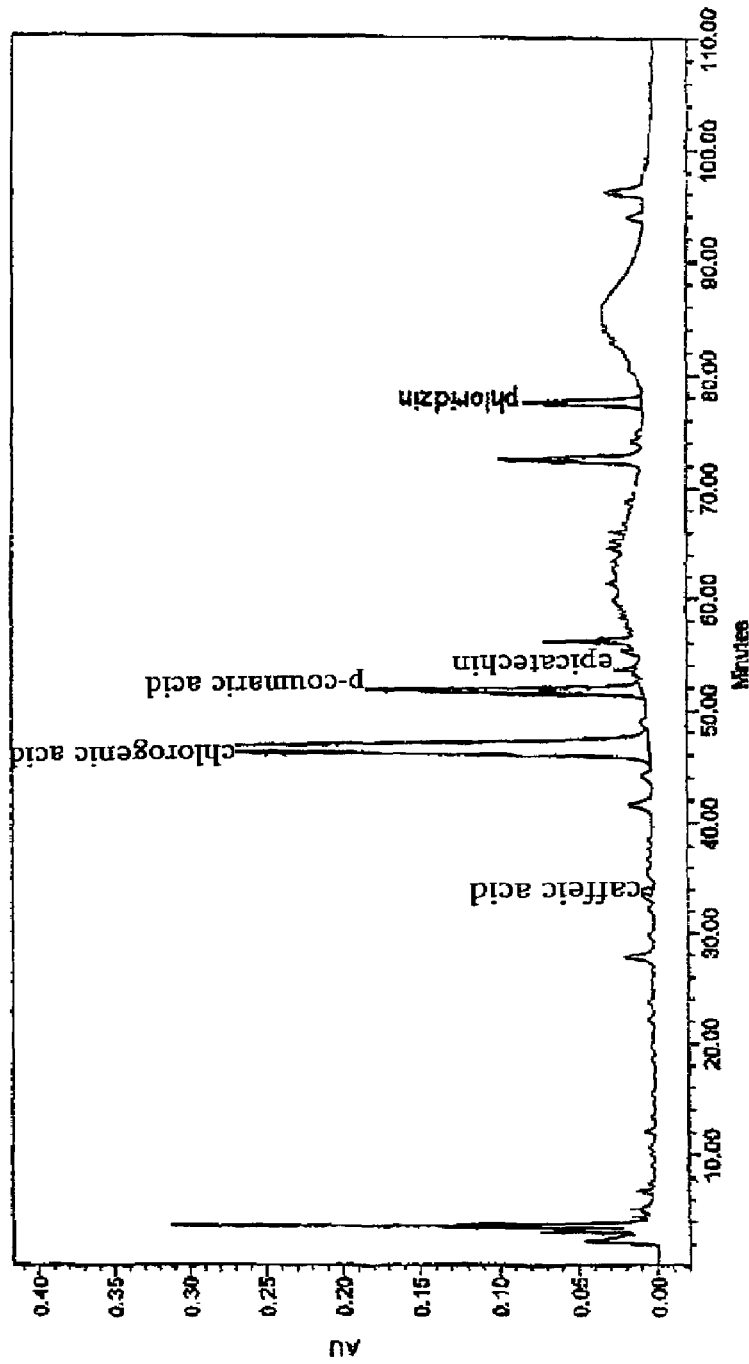
FIG. 1 is an HPLC chromatogram of a cider apple.
Figure 2:
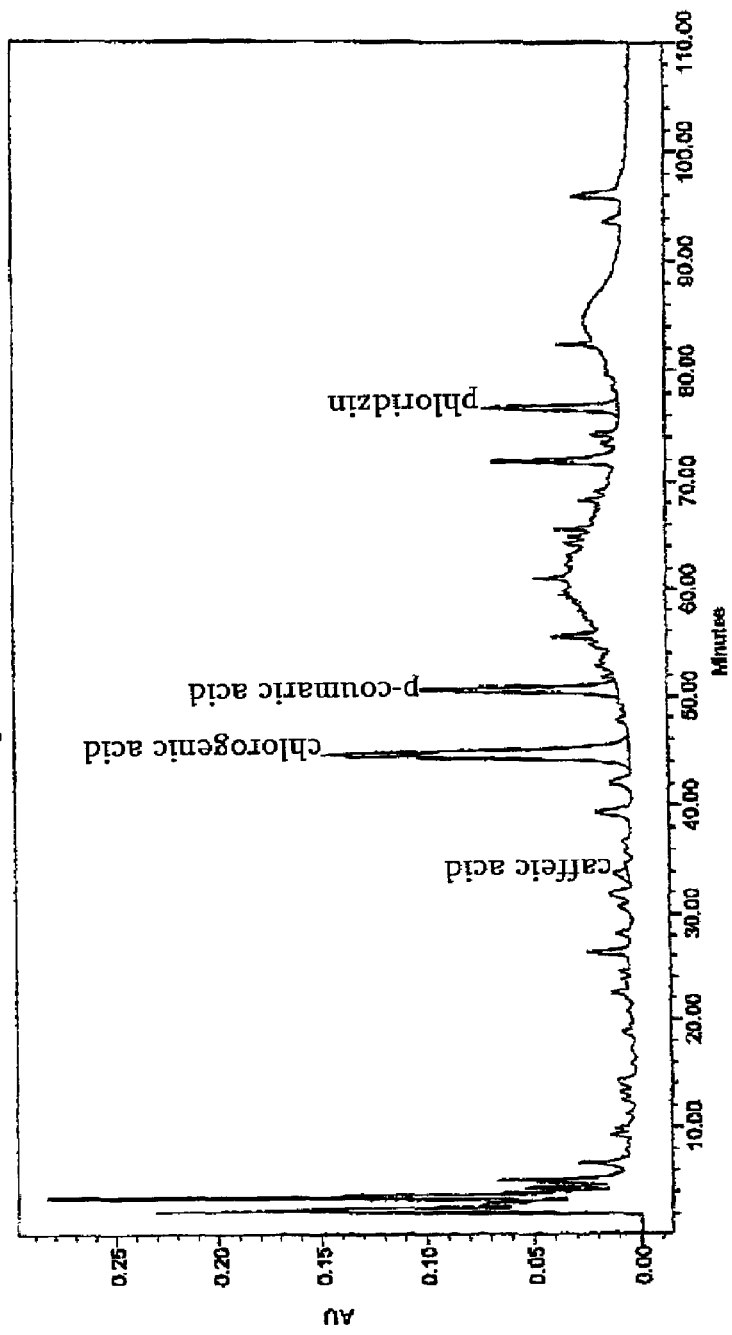
FIG. 2 is an HPLC chromatogram of a dessert apple.
Figure 3:
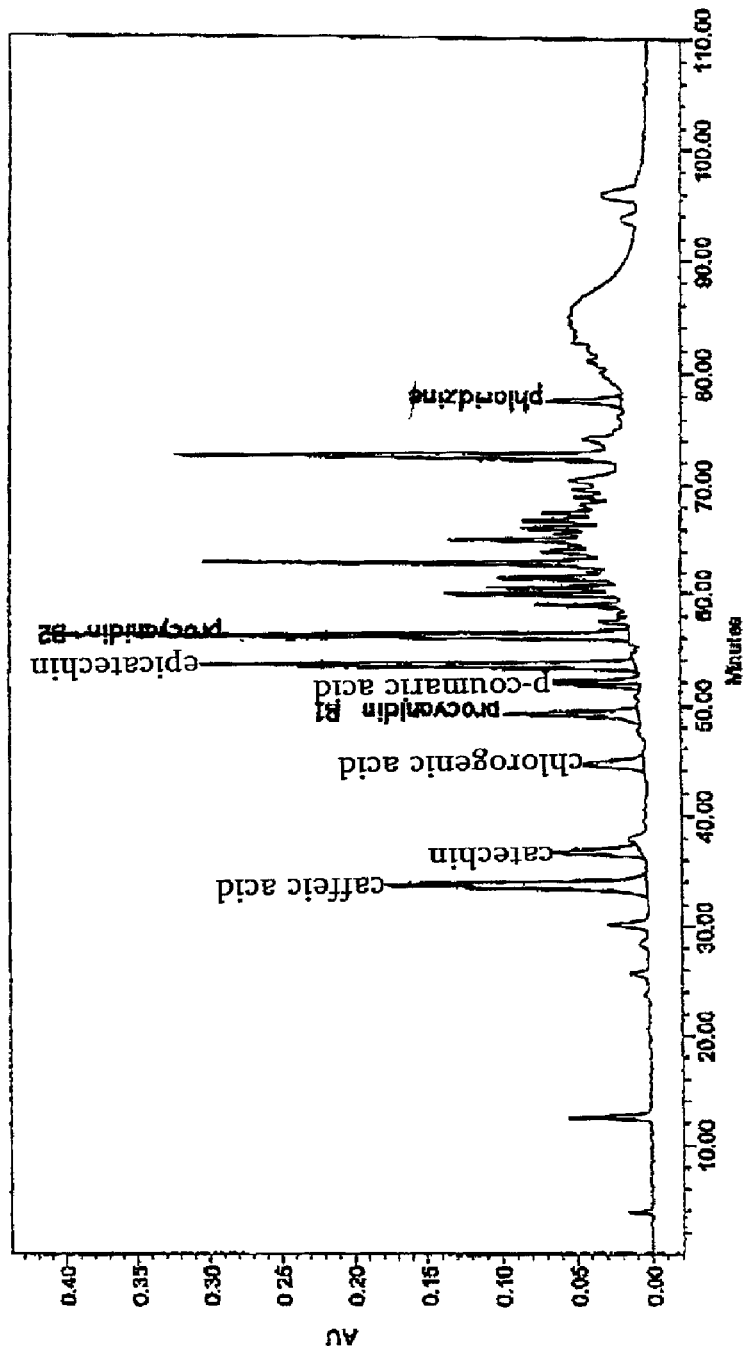
FIG. 3 is an HPLC chromatogram of a conventional polyphenolic extract.

The polyphenolic fraction in accordance with the invention comprises at least 20% by weight of polyphenols and preferably 50%, at least 10% by weight of which is composed of phloridzin, and preferably between 10% and 70%. This extract can also comprise in its composition chlorogenic acid, epicatechin, procyanidin B2, quercitrin, p-coumaric acid and also phloretin.

One composition that is particularly preferred of this polyphenolic fraction is that it contains, by weight:
more than 20% and preferably more than 50% of total polyphenols;
at least 30% and preferably from 30% to 40% by weight of the polyphenols as phloridzin;
not more than 11% and preferably between 2% and 11% by weight of the polyphenols as chlorogenic acid;
not more than 4% of the polyphenols as epicatechin;
not more than 2% of the polyphenols as procyanidin B2;
not more than 1.5% of the polyphenols as quercitrin;
not more than 0.4% of the polyphenols as p-coumaric acid; and
less than 0.2% of the polyphenols as caffeic acid.

Another subject of the invention is that the caffeic acid is present in weight proportions of less than 20% of the weight of phloridzin present. Preferably, the caffeic acid represents less than 1% by weight of the total polyphenols in the extracts. The proportion of phloridzin is 9 times as great by weight as that of the catechin. The amount of phloridzin present is at least equivalent by weight to that of the chlorogenic acid.

Another subject of the invention is characterized in that it contains phloretin. By means of a controlled acid hydrolysis, virtually all of the phloridzin can be converted into phloretin, which is less water-soluble.

Another subject is characterized in that the dihydrochalcones are present in proportions of greater than or equal to 40% by weight relative to the hydroxycinnamic acids.

The extraction process for selectively extracting a dihydrochalcone-rich polyphenolic fraction from ripe apples is characterized in that it comprises the following steps:
the crushed apples are subjected to one or more solid/liquid extractions, in the presence or absence of added water;
the wet solid extract obtained is then either dried or enzymatically liquefied to obtain a liquid extract;
the dry solid extract undergoes further extractions over a period of between 10 minutes and 2 hours with a polar organic solvent, preferably a $C_1$–$C_4$ aliphatic alcohol, pure or as a mixture with water, to obtain an organic extract;
this organic extract is evaporated to dryness at a temperature of less than or equal to 60° C., preferably under reduced pressure;
this residue is then taken up in water, after which it is depleted several times, preferably 4 times, with a water-immiscible solvent, preferably ethyl acetate or methyl or propyl acetate;
the organic solutions obtained are mixed together and evaporated to dryness at a temperature of less than 60° C., and preferably less than 50° C., to obtain the polyphenolic fraction which is the subject of the present invention.

Via another route,
the wet solid extract is mixed with water in the presence of an enzymatic mixture for a period of between 1 and 4 hours at a temperature of between 30 and 50° C., and preferably between 40 and 45° C., to obtain a liquid extract;
this liquid extract is clarified by centrifugation or by filtration and then by ultrafiltration;
the extract is loaded onto a chromatography column filled with an adsorbent resin of styrene-divinylbenzene type. The resin is washed with acidified water to remove the impurities and the residual sugars. The polyphenols are then eluted with an aqueous-alcoholic solution containing between 40% and 70% and preferably between 50% and 60% by weight of ethanol. Other $C_1$–$C_4$ aliphatic alcohols may be used, such as methanol or butanol;
if necessary, a dewaxing step is introduced during the process;
the product obtained by extraction is taken up a final time in water and then dried, preferably by atomization or lyophilization to give a beige-colored powder containing at least 20% by weight of polyphenols, preferably more than 50% of polyphenols, 10% by weight of which, and preferably between 10% and 70% of the polyphenols are dihydrochalcones, preferably phloridzin.

The fractions are obtained by the process described above, preferably from ripe apples of the Rosaceae family and in particular of the species *Malus sylvestris* Mill.

This extract of eating apples having the characteristics stated, obtained according to the process described above, may be used as a dietary or nutraceutical supplement.

The dihydrochalcone-rich phenolic fraction according to the invention has properties as an agent for protecting against ultraviolet radiation, and has antioxidant properties.

A subject of the invention is also a cosmetic composition comprising, inter alia, the dihydrochalcone-rich polyphenolic fraction described above.

The compositions according to the invention may be ingested or applied to the skin. According to the mode of administration, the composition according to the invention may be in any form usually used in cosmetics.

The compositions according to the invention may especially be in the form of gel capsules, milks, lotions, creams, gels or beverages.

The nutraceutical, dietary or cosmetic compositions of the present invention are conventionally formulated according to the applications for which they are intended.

The examples which follow illustrate the invention without limiting it in any way.

EXAMPLE 1

Protocol No. 1 for Extracting the Polyphenolic Fraction of Apple

Apples of the species *Malus sylvestris* Mill. were subjected to the following extraction treatment:

the apples were crushed and the homogenate is stirred in the presence of about 20% water;

the homogenate was subjected to successive solid/liquid extractions to remove the sugar-rich liquid fractions;

the solid extract, which was still wet from the second step, was dried and then treated for a period of 2 hours in a methanol/water mixture in proportions of 90/10 by weight;

the organic extract was evaporated to dryness at a temperature of about 50° C., under reduced pressure;

the evaporation residue was taken up in water and the aqueous solution obtained was then depleted 4 times with ethyl acetate, a water-immiscible solvent;

the organic solutions obtained were mixed together and evaporated at a temperature of about 45° C. to obtain a dry extract; and the dry extract was taken up a final time in water for a final drying, preferably by atomization or lyophilization, to give a fine, beige-colored, partially water-soluble powder.

Figure 4:
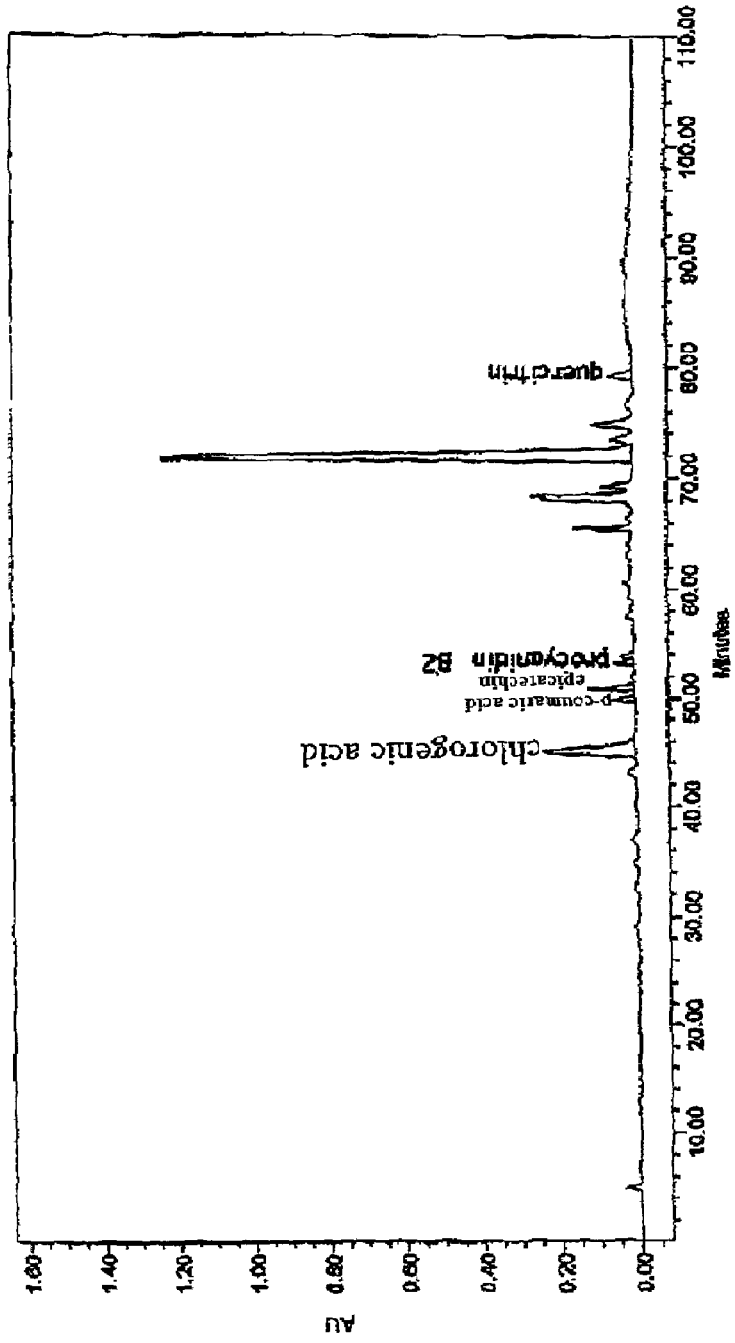
FIG. 4 is an HPLC chromatogram of an extract according to Example 1 of this invention.

The polyphenol composition of this extract, obtained by high performance liquid chromatography measurement of the concentration of each molecule relative to its pure standard, was as follows (FIG. 4).

| Phenolic compounds | Polyphenolic extract according to the invention (in mg/g) |
|---|---|
| Total polyphenols (expressed as phloridzin equivalent) | 492.1 |
| Phloridzin | 196.2 |
| Chlorogenic acid | 55.0 |
| Epicatechin | 20.8 |
| Procyanidin B2 | 11.3 |
| Quercitrin | 7.9 |
| p-Coumaric acid | 2.3 |
| Caffeic acid | <1 |

It is found that the phenolic fraction obtained by this extraction process is particularly rich in phloridzin. It has the characteristic of being poor in acids of the hydroxycinnamic family, and more particularly in chlorogenic acid. It is also poor in acids of the flavanol family (catechins, epicatechins, procyanidins B1, B2, etc.), which leads to an original phenolic profile that is entirely different from those described for apple, and entirely different from a phenolic profile obtained by a standard process using ripe apples.

The powder obtained has a titer of 55% of total polyphenols by weight by the Folin-Ciocalteu colorimetric method, using chlorogenic acid as standard. This method uses the Folin-Ciocalteu reagent (reference 9001, Merck). Briefly, this reagent consists of a mixture of phosphotungstic acid and phosphomolybdic acid, which is reduced during the oxidation of the phenols to a mixture of blue oxides of tungsten and of molybdenum. The color developed is proportional to the content of phenolic compounds present.

Via a chromatographic method and integration of the profile obtained by high performance liquid chromatography, it has a titer of between 49% and 67% of total polyphenols by weight depending on whether the value is expressed as phloridzin equivalent or as chlorogenic acid equivalent, respectively.

EXAMPLE 2

Protocol No. 2 for Extracting the Polyphenolic Fraction of Apple

Apples of the species *Malus sylvestris* Mill. were subjected to the following extraction treatment:

the apples were crushed and the homogenate was stirred in the presence of about 20% water;

the homogenate was subjected to successive solid/liquid extractions to remove the sugar-enriched liquid fractions;

the wet solid extract was mixed with water in the presence of an enzymatic mixture rich in pectolytic, hemicellulasic and cellulasic activities, for about 2 hours at a temperature of about 45° C. to obtain a liquid extract;

the liquid extract was clarified by centrifugation or by filtration and then by ultrafiltration;

the clear liquid extract was then loaded onto a chromatography column filled with an adsorbent resin of styrene-divinylbenzene type;

the resin was washed with acidified water to remove the impurities and the residual sugars;

the polyphenols were then eluted with an aqueous-alcoholic solution containing 60% by weight of ethanol; and the polyphenolic solution obtained was concentrated and then dried by atomization or lyophilization to obtain a fine beige-colored powder.

Figure 5:
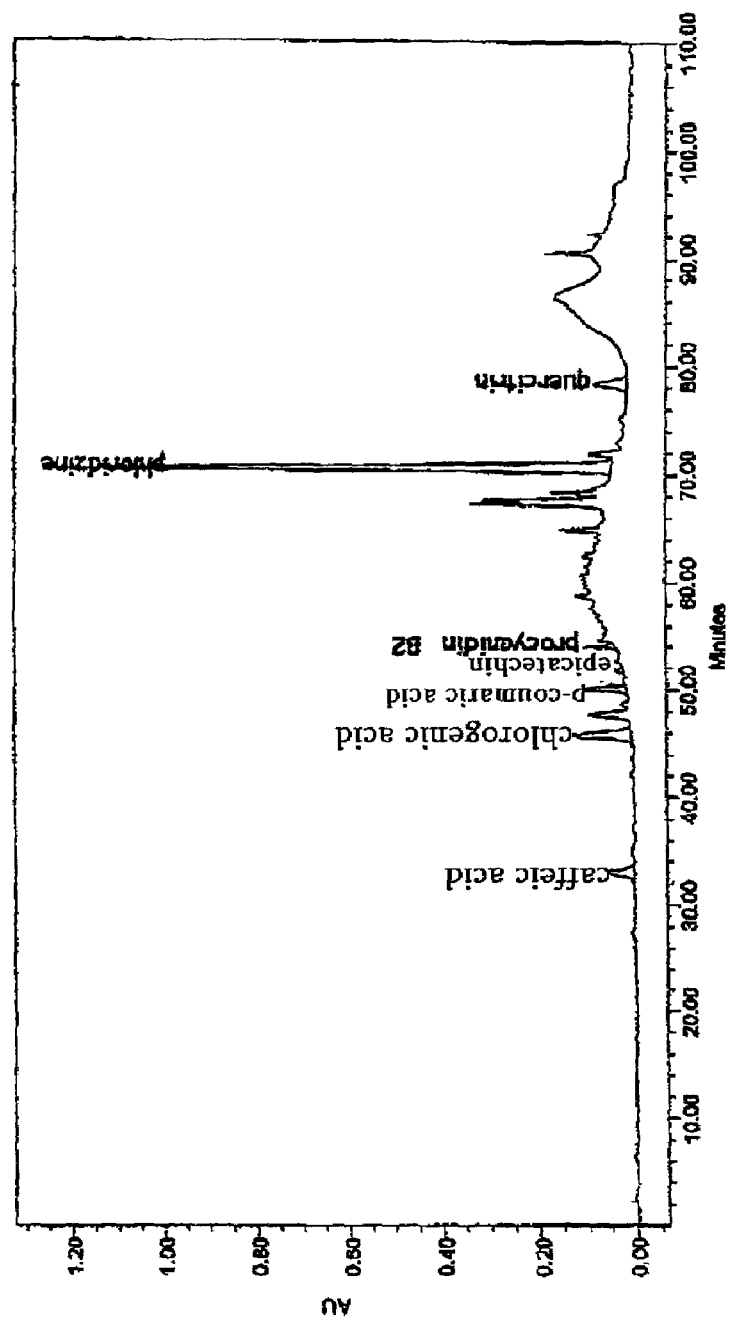
FIG. 5 is an HPLC chromatogram of an extract according to Example 1 of this invention.

The polyphenol composition of this extract, obtained by high performance liquid chromatography measurement of the concentration of each molecule relative to its pure standard, was as follows (FIG. 5):

| Phenolic compounds | Polyphenolic extract according to the invention (in mg/g) |
|---|---|
| Total polyphenols (expressed as phloridzin equivalent) | 293.2 |
| Phloridzin | 36.7 |
| Chlorogenic acid | 7.5 |
| Epicatechin | 1.0 |
| Procyanidin B2 | ε |
| Quercitrin | 3.8 |
| p-Coumaric acid | 1.2 |
| Caffeic acid | 1.7 |

The powder obtained has a titer of 50% of total polyphenols by weight by the Folin-Ciocalteu colorimetric method, using chlorogenic acid as standard.

It is found that the phenolic fraction obtained by this extraction process is particularly rich in phloridzin. As with the extract of Example 1, this fraction has the characteristic of being poor in acids of the hydroxycinnamic acid family and more particularly in chlorogenic acid. It also has the characteristic of being poor in flavanols (catechins, epicatechins, procyanidins B1, B2, etc.), which leads to an original phenolic profile that is entirely different from those described for apple, and entirely different from a phenolic profile obtained by a standard process using ripe apples.

In contrast with Example 1, a small amount of caffeic acid is present, representing only 4% by weight of the amount of phloridzin present.

By integration of the profile obtained by high performance liquid chromatography, it has a titer of between 29% and 40% by weight of total polyphenols depending on whether the value is expressed as phloridzin equivalent or as chlorogenic acid equivalent, respectively.

EXAMPLE 3

Protocol No. 3 for Extracting the Polyphenolic Fraction of Apple

The phloridzin-rich polyphenolic extract according to the invention may be modified before the final drying step. The process consists of a controlled acid hydrolysis in the presence of mineral acid (diluted to a pH of about 3) of phloridzin (phloretin 2'-β-glucoside) into phloretin. The powder obtained after drying is sparingly water-soluble (very low solubility of phloretin) but has advantageous antioxidant activity.

EXAMPLE 4

Antioxidant (or Free-radical-scavenging) Activity of the Phloridzin-rich Polyphenolic Fraction According to the Invention The measurement of the free-radical-scavenging activity of the polyphenolic extracts was performed by the DPPH (1,1-diphenyl-2-picrylhydrazyl) method described by Brand-Williams et al. (1995) and Lu and Foo (2000), slightly modified. Brand-Williams W., Cuvelier M. E. & Berset C. (1995) Use of a free radical method to evaluate antioxidant activity. *Lebensmittel-Wissenschaft und Technologie*, 28, pp. 25–30. Lu Y. & Foo L. Y. (2000) Antioxidant and radical scavenging activities of polyphenols from apple pomace. *Food Chemistry*, 68, pp. 81–85.

The principle is that of measuring the residual amount of DPPH°, a colored radical that is stable under the operating conditions and whose concentration decreases during an incubation in the presence of antioxidant extracts under standardized conditions. Specifically, the extracts with antioxidant activity reduce the DPPH° radical to $DPPH_2$. The antioxidant activity is expressed relative to the activity of a reference molecule, Trolox®, 6-hydroxy-2,5,7,8-tetramethylchroman-2-carboxylic acid (a water-soluble vitamin E analog).

6 mg of DPPH° were carefully dissolved in 100 ml of an aqueous methanol solution at 75 vol %. In parallel, a precise amount of sample to be analyzed and 18 mg of Trolox® were dissolved in 25 ml of 75% methanolic solution. 2 ml of DPPH° solution were incubated with 25 µl of solution to be measured at a temperature of 37±0.5° C. in leaktight flasks for 6 hours. The reduction in the coloring intensity of the solution was measured at a wavelength of 515 nm at t=0 min, t=5 min and t=6 hours. The activity is expressed as mmol Trolox® equivalent/kg of product after incubation for 6 hours.

The DPPH method was used to determine the antioxidant activity of these products:
blood plasma;
red wine;
concentrated red wine extract containing 5% of total polyphenols;
red wine powder containing 55% of total polyphenols;
apple juice;
extract of elderberry containing 40% of total polyphenols (OD 280 nm);
extract of blueberry containing 30% of total polyphenols (OD 280 nm);
phloridzin-rich polyphenolic extract containing 50% of total polyphenols according to the process of the invention;
phloridzin-rich polyphenolic extract containing 90% of total polyphenols according to the process of the invention; and
phloretin-rich polyphenolic extract containing 90% of total polyphenols according to the process of the invention.

| Product | Antioxidant capacity (mmol Trolox ® equivalent/ kg of product) |
|---|---|
| Blood plasma (biological reference) | 20–25 |
| Red wine | 15–25 |
| Concentrated extract of red wine containing 5% of total polyphenols | 680–700 |
| Apple juice | 5–20 |
| Extract of elderberry containing 40% of total polyphenols by weight | 2900–3000 |
| Extract of blueberry containing 30% of total polyphenols by weight | 3500–3600 |
| Phloridzin-rich polyphenolic extract containing 50% by weight of total polyphenols according to the process of the invention | 4000–4500 |
| Phloridzin-rich polyphenolic extract containing 90% by weight of total polyphenols according to the process of the invention | 6000–6500 |
| Phloretin-rich polyphenolic extract containing 90% by weight of total polyphenols according to the process of the invention | 5800–6300 |

From the above results, the phenolic extracts extracted from *Malus sylvestris* Mill. apple according to the process of the invention have free-radical-scavenging or antioxidant activity that is largely superior to that of products known for their antioxidant activity, tested as reference.

EXAMPLE 5

Free-radical-scavenging Effects of Powdered Polyphenolic Fractions

The genotoxicity of a substance is defined as its capacity to generate lesions on genomic or plasmid DNA. The genotoxic agents may be of exogenous nature (ultraviolet radiation, ionizing radiation, chemical substances, etc.) or of endogenous nature (free radicals produced by cell metabolism, etc.).

The free-radical-scavenging effects of the phloridzin-rich polyphenolic fractions obtained according to the process of the invention were measured in vitro by the "3D" test (Damaged DNA Detection, Analytical Biochemistry, (1995), pp. 37–42).

The principle is based on repairing DNA lesions, the damaged DNA being used as a marker of protective efficacy of the test molecules with respect to free OH° radicals: the reduction in lesions observed on the DNA is correlated with the trapping of the free radicals. During the regeneration step, a label (biotin-labeled nucleotide) is incorporated into the DNA and this incorporation, a quantitative indication of the number of repaired lesions, is then revealed by chemiluminescence.

This test carried out on plasmid DNA allows the detection of genotoxic agents at the early stage of the lesion-mutation-cancerization process. Molecules or mixtures with antioxidant or free-radical-scavenging properties, which can thus protect a human cell from oxidative damage caused by reactive oxygenated species (ROSs), can thus be detected.

The protocol was as follows:

the target DNA was adsorbed onto sensitized wells and then incubated with genotoxic agents in the presence or absence of the polyphenolic extract to be tested (dissolved in an ethanol solution at 2% or in DMSO) or in the presence of catechin (control). In this test, the OH° radical produced by homolytic cleavage of hydrogen peroxide was used as DNA-damaging genotoxic agent. The hydrogen peroxide was added to the wells, which were then irradiated with UVB rays (700 J/m$^2$). Furthermore, a positive repair control consisting of a plasmid DNA predamaged with ultraviolet C radiation was added;

a step of washing with ultrapure water and then with a dioxane solution at 20% in ultrapure water for 5 minutes at 30° C. with gentle stirring made it possible to remove the non-specific interactions between the sample and the test, due to the presence of macromolecules such as proteins that may interfere with the repair signal;

a repair step was performed in the presence of purified cell extracts (which contain the active enzymes of the various DNA lesion repair pathways) and of biotin-coupled modified nucleotides (dUTP). The repair of the lesions involved a phase of excision of the lesions followed by a resynthesis of the DNA fragment or of excised bases. During the repair synthesis step, the modified nucleotides were thus incorporated into the DNA;

a step of recognition of the sites for binding the nucleotides to the DNA by binding to the biotin carried by the nucleotides, an avidin molecule coupled to a peroxidase molecule;

a step of revealing the reaction by adding a chemiluminescent peroxidase substrate. The light signal observed and read on the luminometer was proportional to the amount of lesions repaired. A dose effect was observed in the limit from 1 to 15 lesions per 6 kilobases, this being the case for most of the lesions.

The percentage of protection observed in the presence of ROSs was calculated as the relative reduction of the lesional effect due to the OH° species, that is to say:

% protection={[RLU oxidant−RLU (oxidant+sample)]/RLU oxidant}×100 where RLU=relative light units (arbitrary units of quantity of light).

The specific percentage of protection was corrected by the percentage of non-specific inhibition measured on the samples predamaged with UVC. It is an indication of the free-radical-scavenging activity due to the only added extracts.

The $IC_{50}$ is the concentration in mg/ml of test product which gives 50% protective activity against the genotoxic agent OH°. The lower the value, the greater the antioxidant activity of the test product.

| Test product | Concentration (mg/ml) | Specific protection (%) | $IC_{50}$ (mg/ml) |
|---|---|---|---|
| Catechin | 1.00 | 65 | 0.24 |
| (reference molecule) | 0.25 | 52 | |
| | 0.06 | 28 | |
| | 0.016 | 16 | |
| Epicatechin | 1 | 83 | 0.06 |
| (reference molecule) | 0.25 | 71 | |
| | 0.10 | 59 | |
| | 0.010 | 37 | |
| Phloridzin-rich phenolic extract | 0.10 | 75 | 0.05 |
| containing 50% of total | 0.01 | 41 | |
| polyphenols according to the | 0.001 | 17 | |
| process of the invention | 0.0001 | 5 | |
| Phloridzin-rich phenolic extract | 0.10 | 95 | 0.005 |
| containing 90% of total | 0.01 | 64 | |
| polyphenols according to the | 0.001 | 27 | |
| process of the invention | 0.0001 | 7 | |
| Phloretin-rich phenolic extract | 0.10 | 60 | 0.075 |
| containing 90% of total | 0.01 | 23 | |
| polyphenols according to the | 0.001 | 10 | |
| process of the invention | 0.0001 | 1 | |

The three samples have a protective effect with regard to the formation of lesions on DNA by the OH° radicals. They thus have excellent free-radical-scavenging activity, greater than that of epicatechin and very much greater than that of catechin, the two reference molecules that are themselves recognized for their good free-radical-scavenging capacity. A dose-response effect is visible.

The concentrations giving 50% of protective effects are low: about 5 times less of 50% of polyphenolic extract than of catechin is needed for the same level of protection, and about 50 times less of extract containing 90% of phloridzin-rich polyphenols is needed. Low concentrations of polyphenolic extracts as described in the invention are sufficient to result in a marked decrease in the lesional effect of the free radicals. The polyphenolic fractions according to the invention are thus powerful free-radical-scavenging agents which protect DNA in vitro against the genotoxic effects of the OH° radical.

EXAMPLE 6

Antioxidant Effects of Powdered Polyphenolic Fractions

The antioxidant effects of the phloridzin-rich polyphenolic fractions obtained according to the process of the invention were measured on plasmid DNA according to the "3D" test principle described previously. The methodology is the same, the only difference being that, in this test, the genotoxic agent which damages the DNA is singlet oxygen $^1O_2$ produced by illuminating methylene blue.

The principle is based on repairing DNA lesions, the damaged DNA being used as a marker of the protective efficacy of various molecules with respect to singlet oxygen $^1O_2$.

The methylene blue thus illuminated and diluted to 4 ng/ml in ultrapure water was introduced into the wells, which were then irradiated with white light (2×75 W) for 20 minutes. The reference molecule used was silymarin or silibinin (Sigma), a mixture of antihepatotoxic flavonolignans extracted and purified from *Silybum marianum*, which is well known for its detoxifying activity with respect to oxygen.

The results were as follows:

| Test product | Concentration (mg/ml) | Specific protection (%) |
| --- | --- | --- |
| Silymarin | 1 | 74.6 |
|  | 0.1 | 0 |
| Phloridzin-rich phenolic extract containing 50% of total polyphenols according to the process of the invention | 1 | 85.8 |
|  | 0.1 | 0 |
| Phloridzin-rich phenolic extract containing 90% of total polyphenols according to the process of the invention | 1 | 90 |
|  | 0.1 | 81 |
| "Apple industries" concentrated juice with a titer of 1.59 mg TPP/g (polyphenols expressed as phloridzin equivalent) | 100 | 80.3 |
|  | 10 | 77.1 |
|  | 1 | 0 |

TPP: total polyphenols

The extracts obtained according to the invention have antioxidant activity that is about 100 times as high as that of apple juice concentrate (which itself has appreciable activity).

Their activity is comparable to that of silymarin for the phloridzin-rich phenolic extract containing 50% by weight of total polyphenols and ten times as great as that of silymarin for the phloridzin-rich phenolic extract containing 90% by weight of total polyphenols according to the process of the invention.

The polyphenolic fractions according to the invention are thus powerful free-radical scavengers which play an important role in protecting a body subjected to the action of reactive oxygenated species formed by cell metabolism.

EXAMPLE 8

Photo-genoprotective Effect of Powdered Polyphenolic Fractions

The anti-ultraviolet protective role of the phloridzin-rich polyphenolic fractions according to the invention was measured on plasmid DNA according to the in vitro "3D" test principle described previously.

The principle is based on measuring the amount of lesions suffered by the DNA, the damaged DNA being used as a marker of the protective efficacy of test molecules with respect to ultraviolet radiation.

The potentially photo-protective products to be tested were diluted in pure ethanol or ultrapure water and then deposited on an ultraviolet-transparent plate. This plate was then superimposed on that containing the adsorbed plasmid DNA. The assembly was irradiated with ultraviolet B rays at a power of 50 KJ/$m^2$. The reference product used was a commercial product recognized for its protective action against ultraviolet radiation, Parsol® MCX (2-methylhexyl p-methoxycinnamate) from Roche.

A non-specific inhibition (in the absence of ultraviolet radiation) of the repair signal is not possible in this test, since the test product is not in direct contact with the adsorbed DNA at any time.

The $IC_{50}$ is the concentration in mg/ml of test product which gives 50% protective activity against ultraviolet B radiation. The lower the value, the greater the antioxidant activity of the test product.

The results were as follows:

|  | Concentration (mg/ml) | Specific protection (%) | $IC_{50}$ (mg/ml) |
| --- | --- | --- | --- |
| Parsol ® MCX (Roche) | 1 | 64.9 | 0.03 |
|  | 0.1 | 69.1 |  |
|  | 0.01 | 39.2 |  |
| Phloridzin-rich phenolic extract containing 50% by weight of total polyphenols according to the process of the invention | 1 | 49.7 | 1.00 |
|  | 0.1 | 23.0 |  |
|  | 0.01 | 0 |  |
| Phloridzin-rich phenolic extract containing 90% by weight of total polyphenols according to the process of the invention | 1 | 70.1 | 0.40 |
|  | 0.1 | 38.4 |  |
|  | 0.01 | 21.6 |  |
|  | 0.001 | 13.6 |  |
| "Apple industries" concentrated juice with a titer of 1.59 mg TPP/g (polyphenols expressed as phloridzin equivalent) | 100 | 59.0 | 33 |
|  | 10 | 44.5 |  |
|  | 1 | 21.0 |  |
|  | 0.1 | 40.2 |  |
|  | 0.01 | 37.9 |  |

Although less photo-protective than Parsol® MCX, the polyphenolic extracts nevertheless show large anti-ultraviolet B activity.

It may thus be concluded that the polyphenolic extracts as described in the present invention have an appreciable photo-genoprotective effect with respect to ultraviolet B radiation, which is between 30 and 80 times as great as that of a known industrial concentrated apple juice.

The invention claimed is:

1. A fraction obtained from fruit of the Rosaceae family comprising at least 20% by weight of polyphenols, and said fraction comprising at least 10% by weight of phloridzin relative to a total of the polyphenols and wherein chlorogenic acid is present in not more than 11% by weight of the polyphenols.

2. The fraction of claim 1 wherein said fraction comprises from 10% to 70% by weight of phloridzin relative to the total of the polyphenols.

3. The fraction of claim 1 where the weight ratio of phloridzin to chlorogenic acid is greater than or equal to 1.

4. The fraction of claim 1 further comprising caffeic acid wherein the weight ratio of phloridzin to caffeic acid is greater than 4.

5. The fraction of claim 4 where the caffeic acid represents less than 1% by weight of the total of the polyphenols.

6. The fraction of claim 1 wherein the fraction further comprises phloretin, caffeic acid, and p-coumaric acid, and where the sum of the weights of phloridzin and phloretin is at least 40% of the sum of the weights of caffeic acid, chlorogenic acid and p-coumaric acid.

7. The fraction of claim 1 wherein the fraction comprises more than 50% by weight of polyphenols.

8. The fraction of claim 1 in powder form.

9. The fraction of claim 8 wherein the fraction comprises from 10% to 70% of phloridzin by weight.

10. The fraction of claim 1 wherein the fruit of the Rosaceae family is an apple.

11. The fraction of claim 10 wherein the apple is a ripe apple.

12. The fraction of claim 11 wherein the ripe apple is of the species *Malus sylvestris* Mill.

13. The fraction of claim 1 wherein the fraction comprises at least 30% phloridzin relative to the total of the polyphenols.

14. A fraction obtained from fruit of the Rosaceae family comprising at least 20% by weight of polyphenols, and said fraction further comprising at least 10% by weight of phloridzin relative to a total of the polyphenols; wherein not more than 11% by weight of the polyphenols is chlorogenic acid; wherein not more than 4% of the polyphenols is epicatechin; wherein not more than 2% of the polyphenols is procyanidin B2; wherein not more than 1.5% of the polyphenols is quercitrin; wherein not more than 0.4% of the polyphenols is p-courmaric acid; and wherein less than 0.2% of the polyphenols is caffeic acid.

15. The fraction of claim 14 wherein said fraction comprises from 10% to 70% by weight of phloridzin relative to the total of the polyphenols.

16. The fraction of claim 14 where the weight ratio of phloridzin to chlorogenic acid is greater than or equal to 1.

17. The fraction of claim 14 where the weight ratio of phloridzin to epicatechin is greater than 9.

18. The fraction of claim 14 wherein the weight ratio of phloridzin to caffeic acid is greater than 4.

19. The fraction of claim 14 further comprising phloretin.

20. The fraction of claim 14 where the sum of the weights of phloridzin and phloretin is at least 40% of the sum of the weights of caffeic acid, chlorogenic acid and p-coumaric acid.

21. The fraction of claim 14 wherein the fraction comprises more than 50% by weight of polyphenols.

22. The fraction of claim 14 in powder form.

23. The fraction of claim 22 wherein the fraction comprises from 10% to 70% of phloridzin by weight.

24. The fraction of claim 14 wherein the fruit of the Rosaceae family is an apple.

25. The fraction of claim 24 wherein the apple is a ripe apple.

26. The fraction of claim 25 wherein the ripe apple is of the species *Malus sylvestris* Mill.

27. The fraction of claim 14 wherein the fraction comprises at least 30% phloridzin relative to the total of the polyphenols.

* * * * *